(12) United States Patent
Gärtner et al.

(10) Patent No.: US 8,506,299 B2
(45) Date of Patent: Aug. 13, 2013

(54) DEVICE AND METHOD FOR MANUFACTURING DENTAL PROSTHESIS

(75) Inventors: Christian Gärtner, Greifswald (DE); Bernd Kordaβ, Greifswald (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 0 days.

(21) Appl. No.: 10/770,708

(22) Filed: Feb. 3, 2004

(65) Prior Publication Data

US 2004/0219490 A1   Nov. 4, 2004

(30) Foreign Application Priority Data

Feb. 5, 2003 (DE) .................................. 103 04 757

(51) Int. Cl.
*A61C 5/08* (2006.01)

(52) U.S. Cl.
USPC ............................................................ 433/218

(58) Field of Classification Search
USPC .................. 433/218, 69, 73, 24, 213, 214
See application file for complete search history.

(56) References Cited

U.S. PATENT DOCUMENTS

| 5,338,198 | A | * | 8/1994 | Wu et al. ........................ 433/213 |
| 5,975,893 | A | * | 11/1999 | Chishti et al. ...................... 433/6 |
| 6,152,731 | A | | 11/2000 | Jordan et al. ..................... 433/69 |
| 6,322,359 | B1 | | 11/2001 | Jordan et al. ..................... 433/73 |
| 6,621,491 | B1 | * | 9/2003 | Baumrind et al. ............. 345/419 |
| 7,153,135 | B1 | * | 12/2006 | Thomas ........................ 433/213 |
| 2002/0033548 | A1 | * | 3/2002 | Brodkin et al. ................. 264/19 |
| 2002/0102517 | A1 | * | 8/2002 | Poirier ........................... 433/173 |
| 2002/0110786 | A1 | * | 8/2002 | Dillier ............................ 433/213 |
| 2006/0063135 | A1 | * | 3/2006 | Mehl .............................. 433/223 |

FOREIGN PATENT DOCUMENTS

| DE | 19532 171 A1 | 2/1997 |
| DE | 198 28 003 A1 | 1/2000 |
| DE | 198 38 238 A1 | 3/2000 |
| DE | 101 07 451 A1 | 9/2002 |
| DE | 101 11 704 A1 | 10/2002 |
| DE | 101 14 290 A1 | 10/2002 |
| EP | 0 904 743 A2 | 3/1999 |
| JP | 9-238959 | 9/1997 |
| JP | 11-128248 | 5/1999 |
| JP | 2002-523133 | 7/2002 |

* cited by examiner

*Primary Examiner* — Sunil K Singh

(74) *Attorney, Agent, or Firm* — Norris McLaughlin & Marcus, P.A

(57) ABSTRACT

The invention relates to a device and a method for manufacturing a dental prosthesis with which and in which the data records for fabricated teeth are fitted into a virtual model of the oral situation. It is possible to subsequently directly manufacture the denture base or to insert the fabricated teeth in the model.

11 Claims, 1 Drawing Sheet

A)

B)

A) 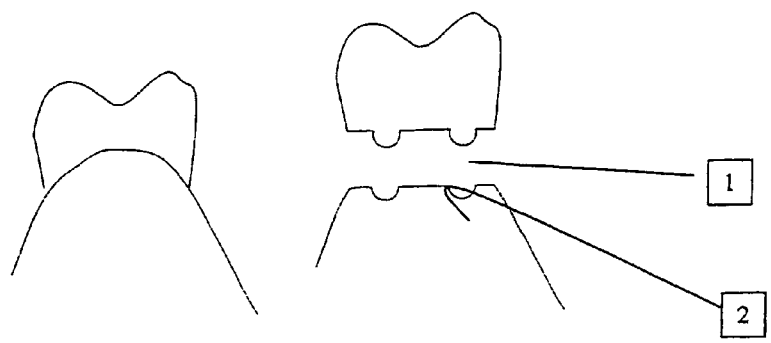
B) 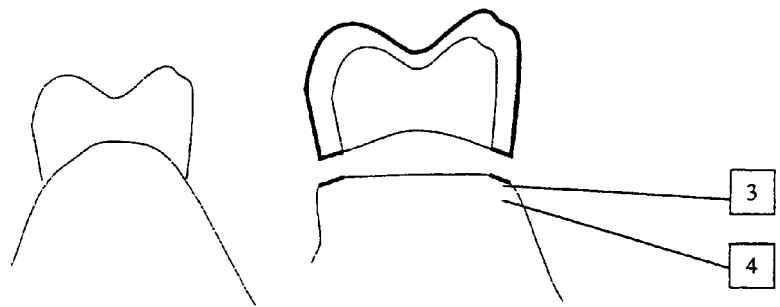

DEVICE AND METHOD FOR MANUFACTURING DENTAL PROSTHESIS

The invention relates to a device and a method for manufacturing a dental prosthesis.

A number of methods are known for the computer-assisted manufacture of dental prostheses, such as milling of ceramic blanks according to 3-D data records (EP 904 743, DE 198 38 238 A1, DE 101 07 451 A1, CEREC® system from Sirona, PROCERA® system from Degussa, LAVA® system from 3M-Espe), or the use of rapid prototyping methods (DE 101 117 04 A1; DE 101 14 290 A1).

It is also known to perform the articulation function totally or partially on the computer, rather than mechanically ("Verbatim," Spring 2000, U.S. Pat. No. 6,152,731 and U.S. Pat. No. 6,322,359).

The object of the invention is to develop a method for manufacturing dental prostheses whereby as much as possible of the entire planning and implementation proceeds in a computer-controlled or computer-assisted manner.

A manufacturing method for dental prostheses is described herein, in which the placement of the teeth is also virtually performed on the computer. The data records for fabricated teeth are fitted into a virtual model of the oral situation. The denture base can be manufactured directly from the subsequentl data, using CAM methods, or the fabricated teeth are inserted in the physical model.

The invention thus relates to a method for manufacturing a dental prosthesis, having the following steps:
a Recording and digitizing (scanning) of the 3-dimensional anatomical relationships in the oral cavity;
b Optional recording and digitizing (scanning) of the 3-dimensional data on bite rims, including occlusion rims;
c Optional recording of mandibular data, which normally is taken on the patient for placement of the articulator;
d Processing of data record D0 from a and optionally b and/or c in such a way that the relevant anatomical structures for virtual placement of teeth are securely affixed, and a virtual model is obtained as data record D1;
e Selection of 3-D data records of fabricated, previously scanned teeth from a data record D3;
f Virtual placement of the teeth into the virtual model, data record D2;
and
EITHER
j Transferring the virtual placement to the model by either a positioning template (for example, milled or rapid prototyped), or direct placement of the fabricated teeth on the model;
k Affixing the teeth to the model;
l Attachment of the denture base;
OR
j Direct manufacture of the denture base, according to the data for the virtual denture placement, with positioning aids for the final correct positioning and affixing of the fabricated teeth.

The method proceeds as follows, by way of example: First, the 3-dimensional anatomical relationships in the oral cavity are recorded in a data record, according to current, common methods. The data may either be recorded directly from the patient, such as with a 3-D camera, a microlaser optical device, a computerized tomography apparatus, or an ultrasound apparatus, or the conventionally prepared plaster model is scanned. The data for optionally present bite rims and occlusion rims may likewise be recorded. It is also recommended that the mandibular data, which normally are taken on the patient for placement of the articulator, be recorded in the system. A data record D0 is thus produced.

Next, the data are prepared in such a way that the geometric relationships relevant for a virtual placement of teeth are present in the computer as a 3-D model. This is referred to below as data record D1.

At this point in the method, the dental prostheses to be used later must be selected by the user. This selection is made from a data record D3, which comprises previously scanned, synthetic prefabricated denture teeth of various sizes and shapes. As a rule the desired tooth shape (such as triangular or square) is selected. The geometric data for the oral situation allow the system to determine the suitable size of the teeth. The prefabricated denture teeth have surfaces which allow an optimal occlusion. A suggestion from the system is then obtained, so that the shape and size as well as the particular distances between the teeth—or also a slightly offset configuration— result in an optimal occlusion for a mandibular movement (data record D2). Inspection of the aesthetic appearance can be performed directly on the screen. It is also possible to generate a frontal view, and to insert this view into the digital photography of the patient's face.

At this point the user has the option to deviate from the optimized model and produce a natural appearance by manually relocating individual teeth and observing the result directly on the screen. For example, using a drag and drop technique the position of an individual tooth can be moved in any desired spatial direction. The system corrects the adjacent and opposing teeth immediately, so that an optimal bite is again produced and a data record D2A is created. The occlusion data for all the opposing teeth may also be edited so that graphic or numerical data are present which evaluate the modified situation as to whether it is more or less favorable than the previous situation. Of course, the previous condition (D2) may be restored if the values are unsatisfactory or incorrect, and then another dental position can be tried out— provided that the aesthetic impression and the occlusion data are satisfactory.

Preferred embodiments of the invention are such that following step f
g Mandibular movements are simulated in/on the computer, and, optionally following step g
h Inspection of the function and occlusion is performed in/on the computer,
and that following step h
i The placement of teeth is manually corrected, and a new calculation is performed to adapt to the determined bite data and optimal occlusion (data record D2A).

In each step of the method it is possible to reconstruct the mandibular movements on the computer in the form of the known virtual articulator.

After the operation on the virtual model is completed, the transfer to the prosthesis can be performed; i.e., a denture base with positioning aids for the teeth is manufactured according to the data for the virtual placement of the teeth. Only the applicable selected prefabricated teeth then need be inserted in the denture base.

The denture base can be directly produced, or a casting mold can be made for the denture base. Methods such as milling or rapid prototyping may be used.

BRIEF DESCRIPTION OF THE DRAWINGS

To ensure an exact fit of the synthetic teeth in the denture base, the following methods, for example, can be used, which are explained with reference to the figures.

FIG. 1A) on the left side shows the desired state, which is affixed according to the virtual placement of the teeth; and on the right side shows the implementation according to the Lego block principle 1 described below;

FIG. 1B) on the left side shows once again the desired state, which is affixed according to the virtual placement of the teeth; and on the right side shows the implementation according to the attachment principle 2 described below.

1. LEGO BLOCK PRINCIPLE (FIG. 1, A):

Specialized structures can be provided at the positions on the denture base on which the synthetic teeth are to be placed. These structures must:
a) Have a defined spatial orientation in six degrees of freedom,
b) Have geometric features which ensure congruence of shape with respect to the particular base for the associated synthetic tooth,
c) Have a design which enables the tooth to be polymer-bonded, adhesive-bonded, or otherwise firmly attached.

As an example, it is possible to prepare a plateau on the denture base which has three hemispherical prominences 1, configured in a triangle, which can be positioned unambiguously in recesses 2 in the denture base congruent thereto. Five degrees of freedom are established by the spatial orientation of the position on the plateau. The prominences are used to define the sixth degree of freedom (rotation about the vertical axis of the tooth). The prominences can be designed so that the teeth may be snapped in, for example by a push-button shape.

2. ATTACHMENT PRINCIPLE (FIG. 1, B):

To avoid modifying the base of the synthetic teeth, a ring-like shape 3 (in the figure, filled in with black in cross section) can be created which exactly matches and defines the geometry of the respective synthetic tooth. The synthetic tooth can be inserted in this attachment so that the spatial orientation of the tooth with reference to the attachment is always constantly defined. In the manufacture of the denture base, corresponding shape-congruent recesses 4 are prepared or opened up which again ensure an exact, defined positioning of the attachment in all six degrees of freedom. Thus, the attachment can be positioned in a defined manner and the corresponding synthetic tooth (including the known spatial orientation with respect to the attachment) can be affixed. After the synthetic tooth is affixed, the attachment can be discarded.

The invention further relates to a device for carrying out the method for manufacturing a dental prosthesis, essentially comprising the following components:
a Scanning or recording apparatus for recording a digital 3-D data record D0 for the oral situation, on the patient or on a (plaster) model,
b Processing device for producing data for a virtual model of the oral situation (data record D1),
c 3-D data record for prefabricated dental prostheses D3,
d Processing module for fitting dental data D3 into the oral situation data D1, with the creation of a virtual model D2 with integrated dental prosthetic teeth (data record D2),
e Simulation module for the mandibular movements (virtual articulator), in which modified positions of the teeth are tested and optimized on virtual model D2,
f Device for manufacturing a positioning template or a denture base from data records D2.

The individual components of the device are explained in detail below:
a The scanning or recording apparatus is, for example, a 3-D camera, a microlaser optical device, a computerized tomography apparatus, or an ultrasound apparatus.
b The processing device for producing data for a virtual model of the oral situation (data record D1) is generally a computer, such as a personal computer, in conjunction with an appropriate program (software).
c The 3-D data record for prefabricated dental prostheses D3 is data originating from the scanning of dental prostheses.
d The processing module is generally a computer program created for this purpose.
e The virtual articulator is, for example, the system described in "Verbatim," Spring 2000.
f Devices for manufacturing a positioning template or a denture base are known, for example rapid prototyping devices.

It should be understood that the preceding is merely a detailed description of one or more embodiment(s) of this invention and that numerous changes to the disclosed embodiment(s) can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. A device for the manufacture of a dental prosthesis comprising:
   (a) a scanning or recording apparatus that produces a digital 3-dimensional recording of an oral situation, on a patient or on a model;
   (b) a processing device that produces from said recording a virtual model of the oral situation;
   (c) a 3-dimensional data record for prefabricated dental prostheses;
   (d) a processing module that fits data for prefabricated dental prostheses into the virtual model and thereby creates a virtual model with integrated dental prosthetic teeth;
   (e) a simulation module that simulates mandibular movements on the virtual model and tests and optimizes positions of the integrated dental prosthetic teeth in the virtual model; and
   (f) a device that manufactures a positioning template or a denture base from the virtual model with the integrated dental prosthetic teeth.

2. A method for manufacturing a dental prosthesis, said method comprising the following steps:
   (a) scanning fabricated teeth to produce 3-dimensional data records of fabricated teeth;
   (b) recording and digitizing 3-dimensional, anatomical relationships in an oral cavity;
   (c) optionally recording and digitizing 3-dimensional data on bite rims;
   (d) optionally recording mandibular data;
   (e) processing data obtained from step (b) and optionally steps (c) and/or (d) in such a way that relevant anatomical structures for virtual placement of teeth are securely affixed, and a virtual model data record is obtained;
   (f) selecting 3-dimensional data records of fabricated teeth;
   (g) virtual placing of the teeth into the virtual model;
   (h) simulating in/on a computer mandibular movements on the virtual model and testing and optimizing positions of the integrated dental prosthetic teeth in the virtual model; and either (k) transferring the virtual placing of the teeth to a model either by a positioning template, or direct placement of the teeth on the model;
(l) affixing the teeth to the model; and
(m) attaching a denture base to the model;

or (n) without carrying out steps (k), (l) and (m), directly manufacturing a denture base, according to data for a virtual denture placement, with positioning aids for a final correct positioning and affixing of the teeth.

3. The method according to claim 2, wherein step (b) comprises recording 3-dimensional, anatomical relationships in an oral cavity with the aid of a 3-dimensional camera.

4. The method according to claim 2, wherein step (b) comprises scanning a plaster model.

5. The method according to claim 2, which comprises following step (h) the following step:
(i) inspecting function and occlusion in/on the computer.

6. The method according to claim 5, which comprises following step (i) the following step:
(j) manually correcting the placing of teeth, and performing a new calculation to adapt the placing of teeth to determined bite data and optimal occlusion.

7. The method according to claim 2, wherein step (k) is carried out, and in step (k) the positioning template is milled or rapid prototyped.

8. The method according to claim 2, wherein step (c) is carried out, and in step (c) the bite rims are occlusion rims.

9. The method according to claim 2, said method comprising the following steps:

(a) scanning fabricated teeth to produce 3-dimensional data records of fabricated teeth;
(b) recording and digitizing 3-dimensional, anatomical relationships in an oral cavity;
(c) optionally recording and digitizing 3-dimensional data on bite rims;
(d) optionally recording mandibular data;
(e) processing data obtained from step (b) and optionally steps (c) and/or (d) in such a way that relevant anatomical structures for virtual placement of teeth are securely affixed, and a virtual model data record is obtained;
(f) selecting 3-dimensional data records of fabricated teeth;
(g) virtual placing of the teeth into the virtual model;
(h) simulating in/on a computer mandibular movements on the virtual model and optionally testing and optimizing positions of the integrated dental prosthetic teeth in the virtual model; and
(n) manufacturing a denture base directly after carrying out step (g), according to data for a virtual denture placement, with positioning aids for a final correct positioning and affixing of the teeth.

10. The method according to claim 2, which comprises following step (h) the following step:
(i) inspecting function and occlusion in/on the computer.

11. The method according to claim 10, which comprises following step (i) the following step:
(j) manually correcting the placing of teeth, and performing a new calculation to adapt the placing of teeth of to bite data and optimal occlusion.

* * * * *